United States Patent [19]

Smith

[11] Patent Number: 6,045,788
[45] Date of Patent: Apr. 4, 2000

[54] METHOD OF STIMULATION OF IMMUNE RESPONSE WITH LOW DOSES OF IL-2

[75] Inventor: Kendall A. Smith, New York, N.Y.

[73] Assignee: Cornell Research Foundation, Inc., Ithaca, N.Y.

[21] Appl. No.: 08/608,516

[22] Filed: Feb. 28, 1996

[51] Int. Cl.$^7$ .................................................. A61K 38/20
[52] U.S. Cl. .................................. 424/85.2; 514/2; 514/8; 514/12; 514/885; 514/886; 514/887; 424/184.1; 424/198.1
[58] Field of Search ........................... 514/2, 8, 12, 885, 514/886, 887; 424/85.1, 85.2, 184.1, 198.1

[56] References Cited

U.S. PATENT DOCUMENTS

| | | | |
|---|---|---|---|
| 4,933,433 | 6/1990 | Tamblyn | 530/351 |
| 4,938,956 | 7/1990 | Howard et al. | 424/85.2 |
| 4,940,456 | 7/1990 | Sibalis et al. | 604/20 |
| 5,126,129 | 6/1992 | Wiltrout et al. | 424/85.2 |
| 5,229,109 | 7/1993 | Grimm et al. | 424/85.2 |
| 5,420,109 | 5/1995 | Suto et al. | 514/8 |

OTHER PUBLICATIONS

Roland Mertelsmann et al., "Treatment of Immunodeficiency with Interleukin–2: Initial Exploration", Journal of Biological Response Modifiers, 4:483–490 (1984) Raven Press, NY.

H. Clifford Lane et al., "Use of Interleukin–2 in Patients with Acquired Immunodeficiency Syndrome", Journal of Biological Response Modifiers, 3:512–516, (1984), Raven Press, NY.

Steven A. Rosenberg et al., "Observations on the Systemic Administration of Autologous Lymphokine–Activated Killer Cells and Recombinant Interleukin—2 to Patients with Metastatic Cancer", The New England Journal of Medicine, (Dec. 5, 1985), pp. 1485–1492.

Yang et al., (1995) Cancer,vol. 76, No. 4, pp. 687–694.

Paul Volberding et al., "Therapy of Acquired Immune Deficiency Syndrome with Recombinant Interleukin–2", Aids Research and Human Retroviruses, vol. 3, No. 2, (1987), pp. 115–124.

Michael A. Caliguiri et al., "Extended Continuous Infusion Low–Dose Recombinant Interleukin–2 in Advanced Cancer: Prolonged Immunomodulation Without Significant Toxicity", Journal of Clinical Oncology, vol. 9, No. 12, (Dec. 1991), pp. 2110–2119.

Michael A. Caligiuri et al., "Selective Modulation of Human Natural Killer Cells in Vivo After Prolonged Infusion of Low Dose Recombinant Interleukin 2", J. Clin. Invest., vol. 91, (Jan. 1993), pp. 123–132.

Gilla Kaplan et al., "The Reconstitution of Cell–Mediated Immunity in the Cutaneous Lesions of Lepromatous Leprosy by Recombinant Interleukin–2," J. Exp. Med., The Rockefeller University Press, vol. 169, (Mar. 1989), pp. 893–907.

David H. Schwartz et al., "Safety and Effects of Interleukin–2 Plus Zidovudine in Asymptomatic Individuals Infected with Human Immunodeficiency Virus," J. of Acquired Immune Deficiency Syndromes, vol. 4, No. 1, (1991) pp. 11–23.

Robert J. Soiffer, "Effect of Low–Dose Interleukine–2 on Disease Relapse After T–Cell–Depleted Allogeneic Bone Marrow Transplantation." Blood, vol. 84, No. 3, (1994), pp. 964–971.

Hedy Teppler et al., "Efficacy of Low Doses of the Polyethylene Glycol Derivative of Interleukine–2 in Modulating the Immune Response of Patients with Human Immunodeficiency Virus Type 1 Infection," The Journal of Infectious Diseases, (1993), 167, pp. 291–298.

Zale P. Bernstein et al., "Prolonged Administration of Low–Dose Interleukine–2 in Human Immunodeficiency Virus–Associated Malignancy Results in Selective Expansion of Innate Immune Effectors Without Significant Clinical Toxicity," Blood, vol. 86, No. 9, (1995) pp. 3287–3294.

Joseph A. Kovacs, M.D., "Increases in CD–4 Lymphocytes with Intermittent Courses of Interleukin–2 in Patients with Human Immunodeficiency Virus Infection," The New England Journal of Medicine, vol. 332, No. 9, (Mar. 2, 1995), pp. 567–575.

Concorde Coordinating Committee, "Concorde: MRC/ANRS randomised double–blind controlled trial of immediate and deferred zidovudine in sympton–free HIV infection," The Lancet, vol. 343 (1994), pp. 871–881.

Yang et al., (1995) Cancer, vol. 76. No. 4, pp. 687–694.

PCT International Search Report.

Morikawa, K. et al., "Enhancement of Therapeutic Effects of Recombinant Interleukin 2 on a Transplantable Rat Fibrosarcoma by the Use of a Sustained Release Vehicle, Pluronic Gel" Cancer Research 47: 37–41, 1987.

Yang et al. (1995) Cancer, vol. 76. No. 4, pp. 687–694.

*Primary Examiner*—Prema Mertz
*Attorney, Agent, or Firm*—Viviana Amzel; Pretty, Schroeder & Poplawski, P.C.

[57] ABSTRACT

A method of activating the immune system of a subject comprises the chronic administration of low doses of an agent such as IL-2, fusion proteins thereof and derivatives thereof that are pharmaceutically acceptable. The agent is provided as a dermal composition, transdermal delivery device and electrotransport device as well as in the form of a kit for self-administration.

60 Claims, 1 Drawing Sheet

FIGURE 1

METHOD OF STIMULATION OF IMMUNE RESPONSE WITH LOW DOSES OF IL-2

BACKGROUND OF THE INVENTION

The present invention was made at least partially with Government funds under Grants Nos. RO1-AI32031-20 and MO1-RR00047. The US Government may have rights in this patent.

FIELD OF THE INVENTION

In the immune system, there are three major types of lymphocytes: B cells, T cells, and natural killer (NK) cells. B-cells are derived from bone marrow, and comprise about 10% of the lymphocytes found circulating in blood. When stimulated by a specific antigen, each B-cell differentiates into a plasma cell that secretes antibodies of a single specificity. T-cells mature in the thymus and, make up about 80% of circulating lymphocytes. Although not producing antibodies, T-cells bear on their surfaces specific antigen receptors resembling antibody molecules. T-cells react to antigen stimulation by secreting immunomediator molecules or cytokines (helper T-cells), and toxic molecules (cytotoxic T-cells). Cytotoxic T-cells act directly on infected cells, and by secreting toxic molecules kill them and any foreign particles, such as microorganisms, they may contain. NK cells, make up about 10% of the lymphocyte population, and are not antigen specific, but recognize and kill cells infected with microbes. Monocytes and macrophages are large scavenger cells that ingest foreign particles and present antigens to the T-cells, which trigger specific immune responses. When an antigen is introduced, it is initially ingested by macrophages and other antigen presenting cells. After digestion, short segments thereof are presented on their cell surfaces. Only a few of all circulating T-cells have receptors that specifically bind to the antigen, and this binding stimulates the T-cells to secrete cytokines.

Cytokines are small proteins secreted primarily, but not exclusively, by cells of the immune system that promote the proliferation and/or differentiative functions of other cells. Examples of cytokines include interleukins, interferons, hematopoietic colony stimulating factors (CSF), and proinflammatory factors such as tumor necrosis factor (TNF). Interleukin 2 (IL-2), one of the first cytokines to be identified and characterized, is produced exclusively by T-lymphocytes in response to stimulation by antigens. IL-2 acts on the three major types of lymphocytes, including T cells, B cells, and NK cells, stimulating them to proliferate and augmenting their differentiative functions. IL-2 potentiates both innate or natural host defenses by stimulating NK cells, and antigen-specific acquired immune reactivity by stimulating T cells and B cells.

In vitro studies have shown that IL-2 mediates its effects by binding to specific receptors (IL-2R) expressed on the surfaces of IL-2-responsive target cells. When IL-2 binds to its receptors, it initiates a series of intracellular events that result in the activation of a set of genes, which products determine the cellular responses observed, such as cellular proliferation. Thus, one of the consequences of IL-2 stimulation is an expansion in the number of T-cells, B-cells and NK cells. IL-2 also stimulates the expression of genes encoding other cytokines, especially by T-cells and NK cells. In particular, IL-2 stimulation of NK cells results in their production of secondary, pro-inflammatory cytokines, including TNFα, interferon γ (IFN), and GM-CSF. These NK cell-derived cytokines, in turn, are potent stimuli for monocytes, promoting their production of further pro-inflammatory cytokines. Thus, although IL-2 is attractive as an immunotherapeutic agent given that it stimulates all of the major types of lymphocytes, its therapeutic use has been impeded by its toxicity, most of which has been attributed to the release of large quantities of secondary cytokines. Clearly, the major problem associated with the administration of IL-2 has been its toxicity, which has prevented its use in therapy for a wide range of illnesses and indications.

Various studies on IL-2 immunotherapy have been reported, and a schematic listing of the most relevant ones is provided in Table 1 below.

TABLE 1

Prior Reports of IL-2 Therapy

| Report | IL-2 Daily Dose ($\times 10^6$ IU/m$^2$) | Admin. Schedule Route | Regime | Side Effects WHO Grade | Immune Function Improv'mt |
|---|---|---|---|---|---|
| Mertlesman '84 | <0.3 | s.q/i.v. | Daily × 21 d | 0? | No |
| Lane '84 | 0.15–15.0 | i.v. | Daily × 5 d/wk × 4 wks | 0? | No |
| Rosenberg '85 | 70 | i.v. | Daily × 5 d/wk × 1–2 wks. | 3 & 4 | ? |
| Volberding '87 | 0.005–9.0 | i.v. | 3 d/wk × 8 wks. | 3 & 4 | Yes |
| Caliguri '91; '93 | 0.05–0.6 | i.v. | Daily × 3 mos | 0 to 2 | Yes |
| Kaplan '94 | 0.1 | i.d. | 2 × Daily × 8 days | 0 & 1 | Yes |
| Schwartz '91 | 1.5–12.0 | i.v. | Daily × 5 d/wk. × 4 wks. | 2 & 3 | Transient |
| Soiffer '94 | 0.2–0.6 | i.v. | Daily × 3 mths. | 1 & 2 | Yes |
| Teppler '93 | 0.18 | i.d. | Daily × 1 mth. | 0 | Yes |
| Bernstein '95 | 0.12–1.2 | s.q. | Daily × 3 mths. | 0 to 2 | Yes |
| Kovacs '95 | 4.0–12.0 | i.v. | Daily × 5 days × 8 wks. | 2 & 3 | Yes | i.v. — Intravenous
s.q. — Subcutaneous
i.d. — Intradermal

The initial reports of therapeutical uses of IL-2 date back to 1984. Since that time, various doses, routes of administration and schedules of administration have been tried. However, up to the present time, IL-2 has only been approved by the Food and Drug Administration for limited use in patients with renal cell carcinoma. For this purpose, the high doses of IL-2 used, only permit its administration for 1–2 weeks before severe toxicity develops. Additional rounds of treatment administered after discontinuance proved ineffective.

Throughout this patent, all reported IL-2 units of biological activity have been converted to International Units (IU) to enable a comparison of the doses of IL-2 used in different studies. An IU is defined as $15 \times 10^6$ units per mg IL-2 protein. In addition, some IL-2 doses are expressed as IU per $m^2$ of body surface area (BSA). The BSA values are easily calculated from similar values based on a subject's weight and height using a standard conversion table of height and weight measurements. For example, a 70 kg. person of normal height has about 1.5 m BSA.

Mertlesman et al. administered daily subcutaneous doses of 1.5 to $3 \times 10^5$ IU impure, natural IL-2/$m^2$ to severely ill AIDS patients. The administration was done by subcutaneous (s.q.) or intravenous (i.v.) injection for a short period of 3 weeks. Neither significant toxicities nor improvement in the measured immunologic parameters were reported. During the same period of time, Lane and co-workers administered daily i.v. doses about 50-fold higher (0.15–$15.0 \times 10^6$ IU impure, natural IL-2/$m^2$) to AIDS patients for 5 days/week, for a short period of time (4 weeks). Again, neither significant toxicity nor improvements in immunologic parameters were reported to occur in this study.

One form of recombinant IL-2 (rIL-2) was administered by Rosenberg and co-workers for the first time in 1985. Cancer patients were treated daily with high doses (up to $70 \times 10^6$ IU rIL-2/$m^2$ given in 3 divided i.v. bolus infusions 5 days/week for short periods of time (1–2 weeks). While this treatment was reported to yield anti-tumor responses in only about 20% of the patients, the dose and schedule of administration led to severe toxicities WHO Grades 3 and 4. (See, Table 3 below). In spite of the severe toxicity elicited, minor variations on these doses and schedules have also been used by others in the past 10 years for the treatment of many malignancies, as well as other indications because of its beneficial anti-tumor responses.

Volberding and co-workers administered i.v. doses of 0.005 to $9.0 \times 10^6$ IU rIL-2/$m^2$ 3 days/week for 8 weeks (a short period of time) to severely ill AIDS patients. Although, no substantial untoward effects were reported at the lower range of dose, toxicities WHO grades 3 and 4 were seen at the higher end of the dose range. In addition, and far more significantly, there was no improvement in the severe immunodeficiencies.

Caliguri and co-workers, including the present inventor, first reported the administration of rIL-2 for a period longer than a few days or weeks to cancer patients. By lowering the daily rIL-2 dose to 0.05 to $0.6 \times 10^6$ IU/$m^2$, IL-2 could be administered for as long as 3 months as a continuous i.v. infusion. A daily dose of less than $0.45 \times 10^6$ IU rIL-2/$m^2$, produced toxicities WHO grade 1, while the highest dose tested, $0.6 \times 10^6$ IU rIL-2/$m^2$/day, produced toxicities WHO grade 2 and higher, requiring the lowering of the dose. A dose of $0.45 \times 10^6$ IU rIL-2$m^2$/day produced a gradual increase in circulating NK cells over a 3-month interval. However, the concentration of circulating T-cells and B-cells failed to increase. The same team (Soiffer et. al.) achieved similar results when treating hematological malignancies in bone marrow transplant patients by administration of a similar dose range and schedule.

Also in 1991, Kaplan and co-workers, including the present inventor, administered doses of rIL-2 in a range similar to that used by Caliguri et al. for only 8 days to patients with lepromatous leprosy. Although this treatment resulted in a 6-fold increase in circulating NK cells, it did not increase the concentration of circulating T cells and B cells. However, marked toxicity WHO Grade 1 was observed.

Schwartz and co-workers administered a 10- to 50-fold higher daily dose (1.5–$12.0 \times 10^6$ IU rIL-2/$m^2$) to asymptomatic HIV+ subjects as a continuous i.v. infusion, 5 days/wk for 4 weeks. Severe toxicity WHO Grades 2 and 3 was reported at these doses, with only a transient improvement in immunologic parameters.

In 1993, Teppler and co-workers, including the present inventor, administered low doses of IL-2 ($0.18 \times 10^6$ IU rIL-2/$m^2$) to asymptomatic HIV+ individuals by daily intradermal (i.d.) injection for a short period (30 days). Although no undue toxicity was observed, only a slight improvement of immune lo function was attained. By comparison, Bernstein and co-workers in 1995 reported administering a slightly higher daily dose (0.12–$1.2 \times 10^6$ IU rIL-2/$m^2$) as a subcutaneous injection for 90 days to severely ill patients with AIDS-associated malignancies. This therapy produced substantial toxicity WHO Grades 1 and 2. In addition, although it increased the concentration of circulating NK cells and eosinophils, it did not lead to increases in T cells or B cells of these end-stage patients.

More recently, Kovacs and co-workers reported treating asymptomatic HIV+ individuals with intermittent high daily doses of 4–$12 \times 10^6$ IU rIL-2 /$m^2$ by i.v. infusion for 5 days with breaks of 8 weeks. This produced severe toxicity WHO Grades 2 and 3. Although transient increases in circulating CD4+T cells were reported, an extremely undesirable larger increase in plasma HIV levels, of up to 50-fold, developed. W094/26293, by the same group, disclosed several intermittent high dose rIL-2 treatments in conjunction with gene therapy, of patients with suppressed immune systems, such as HIV+ individuals. This form of rIL-2 was continously administered by i.v. infusion via central or peripheral lines at a dose of 1–$24 \times 10^6$ IU rIL-2/$m^2$/day for 1 day to 2 weeks, preferably 5 days, with intervals between infusions of 4 weeks to 6 months. However, these doses of rIL-2 are reported to cause severe toxic side effects, including capillary leak with hypotension, high fever (>39° C.), and extreme flu-like symptoms, necessitating hospitalization.

U.S. Pat. No. 5,026,687 discloses the use of ddI for the treatment of HIV+ patients. Example 8 is a paper example which forecasts the oral administration of ddI in combination with an all encompassing dose of IL-2 (25,000–1,000,000 U IL-2/day) by continuous infusion or other systemic administration for a period of 3 months. It is not indicated that these are IU. Although the example indicates that "beneficial results are seen" but, because it is entirely hypothetical, it provides no real information on IL-2 toxicity since no enabling work was provided.

In summary, immunotherapy with high doses (greater than $1 \times 10^6$ IU/$m^2$/day) of IL-2 has been shown to lead to severe, unacceptable toxicity of WHO Grades 2 and higher, requiring hospitalization. These doses are only tolerable for a few days, and result in only transient detectable improvements in immune function. Lower doses of IL-2, i.e., 0.1–$0.5 \times 10^6$ IU/$m^2$/day, have been administered for longer periods of time (up to 90 days) with the production of toxicity WHO Grade 1, only transient increases in immunologic function.

Thus, up until the time of this invention, the view was widely held that the use of IL-2 was contraindicated in patients with HIV infection due to its potential for activating HIV. More generally, up to the present time, no method has been proven to be suitable, effective and safe, for IL-2 immunotherapy of HIV infected individuals for prolonged periods of time in the absence of severe side effects. Nor have there been any reports on the administration of IL-2 to immune impaired infants or mammalian animals, or to normal individuals, infants or mammalian animals which may be temporarily afflicted with an infection or other condition, and who would benefit from a temporary stimulation of their immune system to overcome the condition.

Accordingly, until the present invention, it was not believed possible to administer IL-2, whether in a preventative or therapeutic mode, for prolonged periods of time without eliciting toxicity, so that individuals could carry on normal lives while at the same time experience improved immune function. Moreover, up to the present time IL-2 had never been administered to asymptomatic individuals for longer than 30 days, so that the long-term effects of its chronic administration remained unknown.

In particular, there is still a need for a maintenance method of administering agents having IL-2 activity at a dose which stimulates the immune system, which produces minimal or no toxicity and/or detrimental effects which have precluded the continued administration of the drug, alone and/or in combination with other therapeutic agents. Such method would permit the effective avoidance, and/or amelioration of symptoms, which afflict certain subjects with decreased immune response or an impaired immune system, in a safe manner, permitting them to resume an active life schedule.

SUMMARY OF THE INVENTION

This invention relates to a unit dosage composition, comprising in a sterile container, about 15,000 to 1,000,000 IU of an agent having IL-2 activity, including natural, recombinant and mutated IL-2, analogs and derivatives of IL-2, and to a kit provided with multiple unit dosages of the composition, instructions, and one or more devices for its administration, such as needles and syringes, inhalators, and the like. The composition, may be in various forms, such as creams, ointments, sprays, solutions, suppositories, powders, suspensions, patches, emulsions, and encapsulated particles, among others, and may contain other therapeutic agents, such as additional lymphokines or cytokines, analogues, fragments, fusion proteins, and derivatives thereof, other biologically active agents and formulation additives. Topical and controlled release formulations, implants, inhalators, and transdermal, transbuccal, and transpulmonary delivery devices are also included. The agent may be self-administered by any topical or systemic route, as long as its peptide bonds are protected from degradation.

The present agent is suitable for the chronic stimulation and/or maintenance of immune response in a subject when administered at a dose effective to activate high affinity IL-2 receptors without eliciting substantial toxicity, i.e., WHO Group 1 or higher. The amount of the agent administered may be determined as described herein, and is preferably effective to produce about 10 to about 90% saturation of the high affinity IL-2 receptors. For subcutaneous administration, a daily dose generally falls in the range of about 15,000 to 1,000,000 $IU/m^2$. The present immunotherapy is useful for stimulating the immune system in the prevention and treatment of malignancies, of mild and severe infections afflicting normal individuals, of opportunistic infections generally arising in immunocompromised individuals, such as viral, fungal, parasitic, and bacterial infections, including patients infected with the human immunodeficiency virus (HIV), and infections frequently encountered after operations, such as bone marrow transplants (BMT). The present immunotherapy is also generally suitable for the stimulation of the immune system in normal subjects, and for use in animals in general.

DETAILED DESCRIPTION OF THE PREFERRED EMBODIMENTS

The present invention arose from a desire by the inventor to improve on prior art technology. In the past, short term IL-2 therapy had been attempted with HIV+ patients, with patients suffering from some forms of cancer, and even with patients that had been subjected to bone marrow transplant (BMT). However, high doses of IL-2 were shown to bring about extremely severe side effects, such as those classified by the World Health Organization (WHO) as Grades 1 to Grade 4 toxicities in Table 2 below.

TABLE 2

Recommendations for WHO Grading of Acute and Subacute Toxicity

|  | Grade 0 | Grade 1 | Grade 2 | Grade 3 | Grade 4 |
| --- | --- | --- | --- | --- | --- |
| Hematologic (Adults) Hemoglobin (g/100 ml) | >11.0 | 9.5–10.9 | 8.0–9.4 | 6.5–7.9 | <6.5 |
| Leukocytes 1000/cmm | >4.0 | 3.0–3.9 | 2.0–2.9 | 1.0–1.9 | <1.0 |
| Granulocytes 1000/cmm | >2.0 | 1.5–1.9 | 1.0–1.4 | 0.5–0.9 | <0.5 |
| Platelets 1000/cmm | >100 | 75–99 | 50–74 | 25–49 | <25 |
| Hemorrhage | none | petechiae | mild blood loss | gross blood loss | debilitating blood loss |
| Gastrointestinal |  |  |  |  |  |
| Bilirubin | <1.25 × N* | 1.26–2.5 × N | 2.6–5 × N | 5.1–10 × N | >10 × N |
| SGOT/SGPT | <1.25 × N* | 1.26–2.5 × N | 2.6–5 × N | 5.1–10 × N | >10 × N |

TABLE 2-continued

Recommendations for WHO Grading of Acute and Subacute Toxicity

| | Grade 0 | Grade 1 | Grade 2 | Grade 3 | Grade 4 |
|---|---|---|---|---|---|
| Alkaline phosphatase | <1.25 × N* | 1.26–2.5 × N | 2.6–5 × N | 5.1–10 × N | >10 × N |
| Oral | none | soreness/ erythema | erythema, ulcers, can eat solids | ulcers, requires liquid diet only | alimentation not possible |
| Nausea/vomiting | none | nausea | transient vomiting | vomiting requiring therapy | intractable vomitting |
| Diarrhea | none | transient <2 days | tolerable but >2 days | intolerable requiring therapy | hemorragic dehyd. |
| Renal, bladder | | | | | |
| BUN or blood urea | <1.25 × N | 1.26–2.5 × N | 2.6–5 × N | 5–10 × N | >10 × N |
| Creatinie | <1.25 × N | 1.26–2.5 × N | 2.6–5 × N | 5–10 × N | >10 × N |
| Proteinuria | none | 1 + <0.3 g/ 100 ml | 2–3 + 0.3–1.0 g/100 ml | 4 + >1.0 g/ 100 ml | nephrotic syndrome |
| Hematuria | none | microscopic | gross | gross + clots | obstructive uropathy |
| Pulmonary | none | mild symptoms | exertional dyspnea | dyspnea at rest | complete bed rest req'd |
| Fever-Drug | none | fever <38 C. | fever 38 C.–40 C. | fever >40 C. | fever with hypotension |
| Allergic | none | edema | bronchospasm no parenteral therapy needed | bronchospasm parenteral therapy req'd | anaphylaxis |
| Cutaneous | none | erythema | dry desquamation, vesiculation pruritus | moist desquamation, ulceration | exfoliative dermatitis necrosis requiring surgical intervention |
| Hair | none | minimal hair loss | moderate, patchy alopecia | complete alopecia but reversible | non-reversible alopecia |
| Infection (specify site) | none | minor infection | moderate infection | major infection | major infection with hypotension |
| Cardiac | | | | | |
| Rhythm | none | sinus tachycardia >110 at rest | unifocal PVC atrial arrythmia | multifocal PVC | ventricular tachycardia |
| Function | none | asymptomatic, but abnormal cardiac sign | transient symptomatic dysfunction, no therapy req'd | symptomatic dysfunction, responsive to therapy | symptomatic dysfunction, non-responsive to therapy |
| Pericarditis | none | asymptomatic effusion | symptomatic, no tap req'd | tamponade, tap req'd | tamponade, surgery req'd |

The present inventor has now unexpectedly found that low doses of agents having IL-2 activity, such as natural and recombinant IL-2, active analogues and derivatives of IL-2, or mixtures thereof, may be continuously administered to patients for prolonged periods of time to activate and/or stimulate their immune system in the substantial absence of toxicity. In the remainder of this patent, the narrative will generically refer to IL-2, but the present teachings, unless otherwise indicated, extend to the remainder of the agents encompassed herein.

This invention achieves therapeutic benefits without toxic effects. The effects of the present agents at the IL-2 receptors have been found to be dose-dependent, and to correlate to their binding affinity to the three different receptor classes expressed by different types of cells. The high affinity class, comprised of three peptide chains ($\alpha$, $\beta$, $\gamma$), is expressed by antigen-activated T-cells and B-cells (about $10^7$ cells in the circulation), and by about 10% of NK cells (total circulating about $10^8$ cells). This receptor class is characterized by a very high affinity for IL-2, as expressed by an equilibrium dissociation constant (Kd) of about $10^{-11}$ M. Accordingly, the inventor reasoned that IL-2 concentrations of about $10^{-12}$ M to $10^{-10}$ M M will bind to this class of IL-2R to different degrees. A second class of functional IL-2Rs is comprised of only $\beta$ and $\gamma$ receptor chains, and has a 100-fold lower affinity for IL-2 than the high affinity receptor. This intermediate affinity receptor has a Kd of about $10^{-9}$ M, and is expressed by the majority (>90%) of NK cells (about $10^9$ cells). Thus, IL-2 concentrations which are expected to bind this class of receptors range from about $10^{-10}$ to $10^{-8}$ M. The third class, a low affinity receptor, comprises only $\alpha$ peptide chains, and has the lowest affinity for IL-2, with a Kd about $10^{-8}$ M. In this case, the IL-2 concentrations which are expected to bind to this class of receptor range from about $10^{-9}$ M to $10^{-7}$ M. Although target cells that express only $\alpha$ chains have not been identified, α chains have been detected in the serum as soluble IL-2Rs. However, due to their low IL-2 binding affinity, the soluble low affinity IL-2Rs cannot compete effectively with the cellular high affinity IL-2Rs. Some of the characteristics of the three classes of receptors are shown in Table 3 below.

TABLE 3

IL-2 Receptor Classes

|  | High (M) | Intermediate (M) | Low (M) |
|---|---|---|---|
| Affinity (Kd)* | $10^{-11}$ | $10^{-9}$ | $10^{-8}$ |
| Comp. (Chains) | α, β, γ | β, γ | α |
| Cell Distribution | Activated T & B, ~10% NK | ~90% NK | — |
| IL-2 Conc. | $10^{-12}$ to $10^{-10}$ | $10^{-10}$ to $10^{-8}$ | $10^{-9}$ to $10^{-7}$ |
| No. Responsive Cells | ~$10^8$ | ~$10^9$ | — |

*Kd = equilibrium dissociation constant

The concentration of IL-2, the density of IL-2 receptors on the cell surface, and the duration of the IL-2-receptor interaction are three important parameters in the IL-2 regulation of lymphocyte proliferation and differentiation. A finite number of IL-2-receptor interactions must occur before a cell irrevocably commits to responding by proliferating. In normal individuals the vast majority of circulating T and B lymphocytes, i.e., greater than 99.9%, do not express IL-2Rs and are, thus, IL-2 unresponsive. By comparison, all NK cells express IL-2Rs consitutively, with less than about 10% of NK cells (about $10^8$ cells) expressing high affinity IL-2RS and >90% of circulating NK cells (about $10^9$ cells) expressing intermediate affinity IL-2 Rs. The present inventor has shown that over a prolonged period of time, blood concentrations of about $10^{-12}$ to $10^{-10}$ M IL-2 binding to high affinity IL-2Rs are therapeutic, whereas blood IL-2 concentration in excess of about $10^{-10}$ M, binding to and activating intermediate affinity IL-2Rs expressed by as many as about $10^9$ NK cells, are toxic. Although exemplified for IL-2 itself, suitable doses for all agents in accordance with this invention may be calculated as follows.

Calculation of % IL-2 Receptors Occupied by Different IL-2 Concentrations

Knowing the value of the equilibrium dissociation constant (Kd) of each class of IL-2Rs for IL-2 binding, it is possible to calculate receptor occupancy using the following formula.

$$\% \text{ Receptors Occupied (\% R occ.)} = \frac{[IL-2] \times 100}{[IL-2] + Kd}$$

For example, at a blood IL-2 concentration of $10^{-11}$ M, which is equivalent to the Kd of the high affinity receptors, 50% of high affinity IL-2Rs will be occupied, as may be seen from the following.

$$\% \text{ R occ.} = \frac{10^{-11} M \times 100}{10^{-11} M + 10^{-11} M} = 50\%$$

It thus follows that a blood concentration of about $10^{-10}$ M IL-2 will lead to about 90% occupancy of high affinity IL-2Rs, as is shown below.

$$\% \text{ R occ.} = \frac{10^{-10} M \times 100}{10^{-10} M + 10^{-11} M} = 90\%$$

However, the same blood IL-2 concentration will occupy only <10% of the intermediate affinity IL-2Rs, which have an affinity constant which is 100-fold lower (Kd=$10^{-9}$ M) for IL-2, as may be seen below.

$$\% \text{ R occ.} = \frac{10^{-10} M \times 100}{10^{-10} M + 10^{-9} M} = 10\%$$

Similar calculations may be undertaken for different blood concentrations of IL-2 and other agents and their respective Kds for the three kinds of receptors incorporated in the equation, as shown above.

Determination of Agent's Toxicities Based on % Receptor Occupancy

The WHO grades for the toxicities produced by IL-2 were estimated from the above calculations, in accordance with this invention, and are shown in Table 4 below. They are based upon the World Health Organization (WHO) toxicity grading scale, shown in Table 2 above. Similar estimates may be done as taught herein for all the other agents of this invention.

TABLE 4

Prediction of IL-2 Toxicities

| WHO Toxicity Grade | IL-2 Plasma Concentration (M) | Receptor Occupancy (%) | |
|---|---|---|---|
|  |  | High Aff. Rec. | Intermed. Aff. Rec. |
| 0 | $10^{-11}$ | 50 | 1 |
| 1 | $10^{-10}$ | 90 | 10 |
| 2 | $10^{-9}$ | 99 | 50 |
| 3 | $10^{-8}$ | 99.9 | 90 |
| 4 | $10^{-7}$ | 99.99 | 99 |

In accordance with the invention, the severity of the toxicity is directly related to the blood concentration of IL-2. The latter, thus, together with the Kd value for the ligand-receptor interaction, may be used to calculate the degree of receptor occupancy as described above. If the Kd for the specific ligand-receptor is not known, it may be determined as described above or by other methods known in the art. Thereafter, using the above table, and having measured the peak plasma IL-2 concentration occurring, for example, about 2 hours after a subcutaneous injection, the practitioner may adjust, for example, the dosage of IL-2 for each individual subject. For example, if a given dose yields a peak plasma concentration of $2 \times 10^{-10}$ M, using the above formula, it can be calculated that this concentration will lead to about 95% occupancy of high affinity IL-2 receptors, and more than about 16% intermediate affinity receptors. The dose, therefore, should be reduced gradually to that expected to saturate less than about 90% high affinity IL-2 receptors and less than about 10% intermediate affinity IL-2 receptors.

Figure 1:
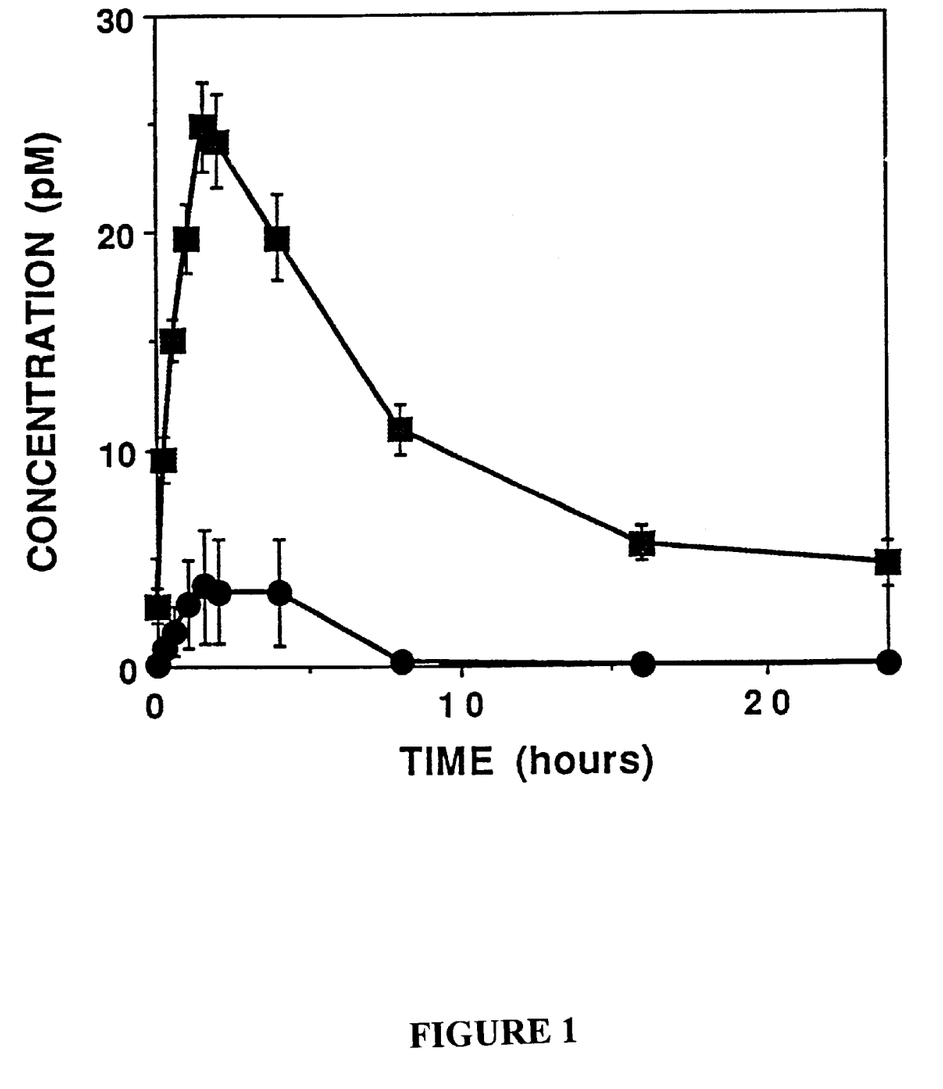
FIG. 1 shows the IL-2 plasma concentration (Mean Standard Error) of samples from 6 subjects who received a daily dose of 125,000 IU recombinant IL- $2/m^2$ (8.3 $\mu g/m^2$)(●), and 8 subjects who received 250,000 IU recombinant IL-2/$m^2$ (16.7 $\mu g/m^2$)(□), assayed at various times over a 24 hour period

One example of the relationship of the IL-2 dose with the peak plasma IL-2 concentration may be seen in FIG. 1, accompanying this patent, which contains data averaged from several subjects administered a recombinant form of the cytokine at two different doses.

Ligand-Receptor Binding Assay

The ligand-receptor binding assay may be conducted, for the different agents in accordance with this invention, as described by Robb et al. (Robb, R., Munck, A., and Smith, K. A., J. Exp. Med. 154: 1455–1474 (1981)). In brief, IL-2 or other ligands must be in their native configuration, and substantially free of contamination by other molecules. The ligand may be labeled, for example, using radioisotopes, enzymes, and other markers. Target cells, isolated membranes, cytoplasm, or nuclei, may then be mixed together with the labeled ligand, and the ligand and receptor allowed to reach a steady state, where the rate of association of the ligand with the receptor about equals the rate of dissociation of the ligand from the receptor. Subsequently, any unbound ligand may be separated from the receptor-bound ligand, usually by centrifuging the bound ligand, and the amounts of the bound and unbound ligand measured, e.g., as described by Robb et al., J. Exp. Med. 154:1455–1474 (1981). The affinity of the ligand-receptor interaction (Kd) may be calculated, as well as the number of receptors per cell, or per weight of cytoplasm or nuclei, from these two experimentally determined values, knowing the number of cells, or amount of membranes, cytoplasm, or nuclei, used.

The data may be plotted by the method described by Scatchard (Ann. NY Acad. Sci. 51: 660–672 (1949). The ratio of bound vs. free ligand may be plotted on the y-axis and the amount of bound ligand on the x axis. The slope of the data points yields the Kd (x/y), whereas the x-axis intercepts yields the number of receptors. Knowing the equilibrium dissociation constant (Kd), the % receptors that will be occupied at each ligand concentration may be calculated as described above.

The dose of agent prescribed herein activates the immune system in a patient, but is non-toxic, so that the subject may carry out normal daily activities. For example, asymptomatic HIV individuals have been shown by the inventor to be able to self-administer daily doses of agent in accordance with this invention safely and without toxicity for prolonged periods of time. The present immunotherapy has been shown effective and free of toxicity WHO grade 1 or greater for a period greater than six months without the occurrence of systemic side effects or significant laboratory abnormalities. In one study reported in the present experimental disclosure, an optimal dose range of a preparation of a specific recombinant IL-2 given to HIV+ individuals was determined to be below 500,000 IU/m$^2$/day. The best effects were attained with doses of about 187,500 IU/m$^2$/day to 250,000 IU/m$^2$/day. (12.5–16.7 $\mu$g/m$^2$/day). However, other agents, including other preparations and other forms of IL-2, and other formulations may have optimal daily doses including higher upper limits, lower low limits, or both, than the exemplified rIL-2 form utilized in the reported study. At this daily dose, the HIV RNA levels in plasma did not change significantly from base line values. Significant stimulation of the immune system, however, was evidenced by substantial increases in circulating NK cells, eosinophils, monocytes, and CD+4 T-cells. More generally, the present immunotherapy may be extended for one or two years, or longer periods, or be administered continuously as a maintenance therapy.

Some of the toxicities monitored to determine a suitable dosage for the recombinant IL-2 utilized in the reported study include weakness, fatigue, lethargy, myalgia, and low grade fever. These symptoms usually occurred within a few days after beginning the recombinant IL-2 injections. In the study presented below, the problem of toxicity observed at high IL-2 doses was circumvented by stopping therapy. The patients were then placed on a lower daily IL-2 dose, which proved safe. No toxicities to major organ systems were detected by laboratory assays throughout the full period of the test reported in this patent. All patients were, therefore, able to self-administer IL-2 daily, and perform normal activities without any hindrance associated with IL-2 side effects.

The low dose IL-2 administered in accordance with this invention does not trigger a burst in viral production of HIV reported previously upon the i.v. administration of high dose of IL-2. For example, increases as high as 50-fold persisting in plasma HIV levels were reported after a daily administration of $4 \times 10^6$ to $12 \times 10^6$ IU/m$^2$ IL-2 for 5 days. In accordance with this invention, an increase in viral production of that magnitude is due to the presence of pro-inflammatory cytokines, which are also responsible for the toxic symptoms observed with high dose IL-2 administration. By way of comparison, the present immunotherapy utilizes approximately 50-fold lower daily doses of IL-2, which do not result in a significant increase in plasma viral levels when compared with pre-treatment levels. Further yet, no opportunistic infections or malignancies are observed in any of the individuals receiving low doses of IL-2.

The substantially lower doses of IL-2 utilized herein, when administered on a daily basis, stimulate the immune system, and significantly increase the number of circulating NK cells, eosinophils, monocytes, and CD4+ T cells. When, prior to this invention, high doses of IL-2 were administered by others as described above, i.v. intermittently every 2 months, it produced only transient increases in CD4+ T cells after each injection and the number of circulating NK cells, eosinophils and monocytes remained unchanged.

One group of cells believed to be critical to the overall immune response, the NK cells, were stimulated by the present method. The number of NK cells increased, on the average, about 7-fold, from 67±12 cells/mm$^3$ prior to therapy to 464±187 cells/mm$^3$ after 6 months of IL-2 therapy in accordance with the invention. The total number of NK cells circulating in 5 l of blood increased from $3.4 \times 10^8$ to $2.3 \times 10^9$ cells. When NK cells are stimulated in vitro with IL-2, they become increasingly cytotoxic, and secrete cytokines that are potent stimuli for monocytes and macrophages. In vivo, the IL-2-promoted accumulation of circulating NK cells increases their cytolytic capacity and the release of secondary cytokines important in the recruiting and activation of monocytes and macrophages. The latter cells play a prominent role in an individual's natural (innate) immune responses. In addition, the augmentation of antigen processing and presentation by monocytes and macrophages, promoted by NK cell-derived IFN-$\gamma$, can augment antigen-specific, acquired immunoreactivity. Therefore, the increased number of circulating NK cells and monocytes elicited by the present immunotherapy contribute to improve both innate and acquired host defenses.

The daily administration of IL-2 in accordance with the invention also elicited a progressive accumulation of circulating CD4+ T-cells in all individuals, with a mean monthly gain of about 26 cells/mm$^3$ blood. In contrast, the intermittent administration of high doses of IL-2 was reported in the literature to lead to only a transient increase in CD4+ T-cell counts in 6 out of 10 subjects. Based on the mean monthly gain in CD4+ T-cells/mm$^3$ observed in the present study extending through six months, an increase of greater than about 300 cells is likely in the CD4+ T-cell count throughout a whole year of therapy. In comparison, when the antiviral agent zidovudine (250 mg, 4 times daily) was administered, the monthly rate of increase in CD4+ T-cells during 6 months of treatment was only 4 cells/mm$^3$ (Seligmann et al. The Lancet 343:871–81 (1994)) versus a 26 cells/mm$^3$ increase by the present method. The HIV protease inhibitors ABT-538 and L-735,524 were recently reported to increase the CD4+ T-cell counts by 240 cells/mm$^3$ over the first month of therapy. However, their administration leads to a rapid development and selection of drug-resistant mutants, and to the return of the CD4+ T-cell count to baseline in two months, even while therapy continued. (Wei et al., Nature 373:117–22 (1995); Ho et al., Nature 373:123–6 (1995)).

The present invention, thus, provides a novel and effective method of stimulating the immune system of a subject by administering to the patient a daily dose of an agent having IL-2 activity, such as natural IL-2, an agent having active analogues, and derivatives thereof, which is effective to activate high affinity IL-2 receptors without eliciting substantial toxicity WHO grade 1 or higher.

Various compositions are provided herein for the administration of the agent of the invention under the conditions prescribed herein. One of them is a topical composition, which in addition to the agent comprises a carrier or diluent for the agent, which is suitable for its transdermal delivery and optionally one or more of a variety of agents suitable for the preparation of different formulations, which will be selected in accordance with the type of formulation and route of administration desired. Examples of these ingredients are buffers, salt forming acids and bases, perfumes, colorants, emollients, adjuvants, single or multiple enteric coatings, copolymers, microporous or semi-permeable membranes, enzyme inhibitors, mucoadhesives, chelating agents, particulate systems, viral envelope proteins, liposomes and other micelles, emulsifiers, lipoproteins and other fatty acid derivatives, surfactants, bile salts, hydrophilic, neutral, and hydrophobic polymers and co-polymers, hydrogels, biodegradable polymers and co-polymers. The composition may also contain additional bioactive agents such as additional lymphokines or cytokines, and active analogues, fragments, fusion proteins, and pharmaceutically acceptable derivatives thereof, anti-bacterial, anti-viral, anti-fungal, anti-parasitic, anti-metabolic, anti-inflammatory, vasoactive, anti-neoplastic, bronchodilating, local anesthetic, immunomodulating, growth promoting and regenerating agents, enzymatic, hormonal agents, neurotransmitters, and cell receptor proteins and ligands. This composition may be in the form of a cream, an ointment, a solution, a gel, a powder, a suspension, an emulsion, encapsulated particles, or mixtures or combinations of these forms. The agent may be present in different amounts, typically the dermal composition has about 0.001 to 50 wt % or more, and preferably about 0.1 to 30 wt %. However, other amounts larger and smaller are also suitable. Another preferred form of the composition is in the form of a controlled release composition wherein the formulation ingredients added control the rate of release of the agent. These may be degradable polymers and copolymers, matrixes which "leach out" the agent, and the like, as is known in the art. The composition may also be produced in the form of an implant for releasing a desired amount of the agent over a pre-determined period of time. The composition of the invention may be provided as a kit with instructions for its use, particularly in terms of the any necessary manipulations, the number and timing of the applications, and the area to be applied to, as well as the frequency taking into consideration different body surface area and weight of the subject. This is particularly important when it is applied or administered to children, and more importantly to infants and newborn babies, as well as to small animals. Smaller doses may be required in these cases. The composition may be delivered from a passive transdermal delivery device formed from a solid support with a compartment containing a solution or suspension comprising the composition. The compartment has a permeable side which is applied to an area of a subject's skin or dermis and the agent is allowed to pass from the device onto and through the skin, mucosal, or buccal surfaces of the subject. The device is preferably placed in a sealed sterile container immediately after manufacture by methods known in the art. A removable cover may be placed on the permeable side of the container prior to sealing and/or packaging to retain the solution or suspension of the agent during storage and prior to use.

This device may be in the form of an electric transport device which also contains donor and counter electrodes, an external power source, and control circuitry. This device may also be in the form of an ultrasound device which also contains an ultrasound generator (transducer), an external power source, and control circuitry. Such devices are known in the art and need not be further described herein. The solution or suspension containing the agent requires the presence of electric conducting agents which will aid in the transport of the electrical current which facilitates the passage of the agent from the solution onto the skin or dermis and through it. In the case of protein such as the present agent, it becomes important to provide means of administration that will not degrade or hydrolyze the peptic bonds, in order to preserve the activity of the agent. In this respect, the topical application of the agent in the form of a multiplicity of formulations is ideally suited to avoid the hydrolyzing conditions of the gastrointestinal tract while providing a direct passage, after the agent is absorbed through the skin or mucous tissue, directly into the blood stream.

Another particularly useful form of the invention is a unit dosage composition, which may be packaged in a sterile container, having about 15,000 to 1,500,000 IU, preferably up to about 1,000,000 IU, more preferably up to about 750,000 IU, and still more preferably up to about 500,000 IU, and as low as about 20,000 IU, preferably as low as about 50,000 IU, and still more preferably as low as about 60,000 IU of the agent of the invention, such as IL-2, pharmaceutically acceptable analogues and derivatives thereof, or mixtures thereof. Examples of these are natural and recombinant IL-2, fusion proteins, PEG, carbohydrate, lipid, therapeutic agent, reduced, non-glycosylated, and mutated derivatives thereof, although others are also contemplated herein. The unit dosage composition may be prepared in any form to deliver the agent. Examples are powder, tablet, capsule, dragee, cream, solution, suspension, emulsion, gel, spray, or liposomal or other micellar forms. Preferred are solid, particularly freeze-dried, and liquid forms. Also preferred are other forms such as those suitable for injection, topical application, controlled release products, inhalation, and others. Examples of controlled release products are transdermal and intradermal devices, slow release oral formulations, patches, skin, mucosal and transbuccal implants, suppositories, and the like. Implants are preferred for long term delivery of the agent. Controlled release products may be prepared as is known in the art and designed for releasing desired amounts of the agent over a pre-determined period of time. In most instances, the amount of the agent contained in the control release product is substantially higher than the desired daily dose. In some cases, the product may contain sufficient amounts of agent for releasing a daily dose over a period of days, weeks, months, and even years. The product may be tested, and the amount of agent to be released adjusted in accordance with the observed absorbed dose. The daily dose administered is preferably about 15,000 to up to about 1,000,000 IU/m$^2$ body surface. The upper daily dose limit is preferably not higher than about 900,000 IU/m², still more preferably not higher than about 800,000 IU/m², and even more preferably not higher than 450,000 IU/m². The lower limit for the daily dose is preferably no lower than about 30,000 IU/m², more preferably no lower than about 45,000 IU/m², and even more preferably not lower than about 100,000 IU/m². However, the slow release of higher or lower amounts of the agent are also contemplated herein. Any of the forms for administration of the agent may also contain other formulation components and additional bioactive agents as described herein.

The agent of this invention may also be administered from an inhalant device, including those utilized to introduce therapeutic or preventative agents into the lungs, as is the case of transpulmonary administration to asthmatic patients. Such devices are known in the art and available commercially. All types of products and compositions which are part of this invention may be provided as a kit, and preferably as a self-administration kit, primarily comprising, in separate sterile containers, a number of unit dosage compositions, and detailed instructions for use of the kit, and optionally, one or more devices including syringes and needles, transdermal, transbuccal, or intradermal patches or implants, or inhalators, for delivering the agent, and a carrier diluent. These devices may be placed in sterile containers, and the entire kit may be contained in a case for marketing and distribution.

The compositions and products provided herein may all be utilized for stimulating and thereafter maintaining the stimulation of the immune system of a mammalian animal by chronically administering the agent of the invention in the form of a composition over a prolonged period of time in an amount effective to activate the high affinity IL-2 receptors without eliciting any substantial toxicity WHO Grade 1 or higher. The present inventor, for the first time, found a manner to stimulate and maintain the stimulation of the immune system of a mammalian animal or a human without interfering with his/her normal activities or producing undesirable side effects which lower the quality of life of the individual. The present immunotherapy may be administered for six months, one year, and for periods in excess of these times as long as parameters, including systemic symptoms of fatigue, malaise, myalgia, fever, and other symptoms typical of overstimulation of intermediate and low affinity IL-2 receptors shown in Table 1 above, are monitored. In general, the amount of agent administered should be effective to produce about 10 to 90% saturation, preferably about 20 to 85%, more perfectly about 30 to 80%, and still more preferably about 50 to 70%, and in some cases below about 60% of the high affinity IL-2 receptors. However, in some cases, no toxicities are elicited even at agent occupancy greater than about 93%, and even 95%. This is generally attained through a dose of about 15,000 to 1,000,000 IU agent/m² body surface/day, and the other preferred doses described above. The composition may be administered by topical and systemic routes, including subcutaneous, intramuscular, intradermal, intralymphatic, intratumor, transdermal, intradermal, intracavitary, oral, intranasal, intravaginal, intraanal, intrabuccal, transbuccal, transpulmonary, or sublingual routes, or by inhalation or implant. Typically, the implants may be placed in the following areas: the limbs, thorax, abdomen and back, and the topical application, particularly when administered by means of a device, may be typically applied to the same areas.

The present immunotherapy may be applied as a preventative or therapeutic treatment to a variety of conditions. At no time in the past has IL-2 or any of the other agents disclosed herein having IL-2 activity been utilized to boost the immune system of normal animals or humans, including children. The present technology may be utilized in humans as well as all types of mammalian animals, including equines, bovines, ovines, large and small animals in the care of a veterinarian, and animals found in the wild, among others. In fact, the present invention extends to the preventative administration of the agent to normal subjects, for example in cases of travel to areas of the country or the world affording the possibility of a contagious infection, and even in the case of the common cold or flu that afflicts many people during the winter months. The present immunotherapy is also applicable to the prevention and treatment of viral, bacterial, fungal and parasitic infections in general, congenital or acquired immunodeficiencies and cancers or other malignancies such as carcinomas, melanomas, sarcomas, leukemias, lymphomas, and myelomas, among others. In many instances, immunotherapy with the agent of the invention prevents increases in malignant cell mass or count, and in some instances, it even produces a reduction in tumor mass.

Other parameters that may be monitored in order to adjust the dose of the agent administered daily are the blood cell count of circulating lymphocytes, monocytes and polymorphonuclear leukocytes, such as T-cells, B-cells, NK cells, monocytes, eosinophils, neutrophils, basophils, antigen-presenting cells, among others. In the case of viral infections, particularly in the presence of the human immunodeficiency virus, one of the ways to determine an adjustment in the dose administered to an individual is to monitor the count of circulating microorganisms. The present immunotherapy does not increase the count of circulating virus or other opportunistic microorganisms when administered over a prolonged period of time, and in some cases it even decreases their count. When the immunotherapy is applied to subjects afflicted with cancer, it is useful to monitor the size of the malignant cell mass or count. This therapy may be administered as the main cancer therapy in the indicated types of malignancies or after surgery, chemotherapy or radiotherapy. In the case of HIV+ or AIDS patients, the present immunotherapy may encompass, in addition to the agent, nucleic acid analogues, other anti-viral drugs, and enzyme inhibitors, in amounts known in the art. Particularly preferred are formulations containing one or more anti-viral agents of the nucleic acid analogue class and one or more protease inhibitors. The agent may be administered in the same formulation with these agents or by a different route. Different drugs may be alternated while the agent of the invention is administered over a prolonged period of time. When specific drugs for which there is no established dose in the art are combined, the combined immunotherapy in accordance with this invention should be started by lowering the dose of each individual drug and then progressively increasing their doses one at a time while monitoring the effect produced on one of more of the parameters followed, as described above. An artisan with average skill in the art of medicine or veterinary science would know how to proceed to attain a desirable combination dose.

In one preferred mode, the agent may be self-administered by the human subject, preferably subcutaneously, transdermally, intrapulmonarily, transbuccally, or by implant. However, for specific types of patients or applications other forms are also preferred. The present treatment is suitable for application to a variety of conditions, which benefit from the stimulation of the immune system. For example, the administration of low doses of the agent of this invention, as described herein, produces an increase in one or more of a group of circulating immunity-building cells, such as lymphocytes, monocytes and polymorphonuclear lymphocytes, including T-cells, particularly CD4+ T-cells, B-cells, natural killer (NK), eosinophils, monocytes, basophils, and antigen-presenting cells. One specific type of recombinant IL-2 has now been shown, in a clinical trial described below, to enhance the concentration of, for example, circulating NK cells, monocytes, eosinophils and CD4+ T-cells.

Suitable anti-viral agents are any of the agents utilized in the treatment of viral infections. Examples are zidovudine (AZT), 2',3'-dideoxyinosine (ddI), 3'-azido- 2', 3'-dideoxythymidine, acyclovir, 1, 3-dihydro-2-propoxymethyquanine (gancyclovir), ribavirin, dideoxycytidine (ddC), lamivudine (3TC), enzyme inhibitors, such as protease inhibitors, e.g., saquinovir, and invirase, among others, and combinations thereof. Preferred are combinations of one or more nucleic acid analogues and one or more protease inhibitors. The anti-bacterial agent may be any one agent known to be effective against the agent associated with the infection. Examples are pentamidines, trimethoprim-sulfamethoxazole, sulfonamides, penicillins, cephalosporins, aminoglycosides, tetracyclines, chloramphenicols, and combinations thereof. Any specifically targeted antibodies and their fragments are suitable for use herein to deliver molecules attached to them to specific sites. Examples are radioisotope, enzyme, toxin, and other therapeutic agent-carrying monoclonal antibodies, and combinations thereof. Any anti-fungal agent is suitable for use herein. Examples are flucytosine, amphotericin B, fluconazole, griseofulvine, and combinations thereof. Any anti-parasitic agent is suitable for use herein. Examples are pyrimethamine, quinacrine, thiabendazole, levamisol, and combinations thereof. Any anti-metabolic agent may be utilized herein. Examples are purine analogues, folic acid analogues, pyrimidine analogues, and combinations thereof. Any anti-inflammatory agent is suitable for this invention. Examples are steroidal anti-inflammatory agents, non-steroidal anti-inflammatory agents such as acetaminophen, aspirin, and combinations thereof.

In addition, vasoactive agents such as epinephrine, norepinephrine, dopamine and combinations thereof, bronchodilating agents such as $\beta_2$ receptor agonists, and combinations thereof, local anesthetic agents such as procaine, cocaine, and combinations thereof, growth promoting and regenerating agents such as epidermal growth factor, fibroblast growth factor, and combinations thereof, additional lymphokines or cytokines such as interleukins other than IL-2, interferons, and the like, hematopoietins, growth factors, hormones, chemokines, active analogues, fragments, fusion proteins and pharmaceutically-acceptable derivatives thereof, and combinations thereof, agents such as soluble CD4 and analogues thereof, anionic polysaccharides, and anti-neoplastic agents such as alkylating agents, anti-metabolites, hormones, vinca, alkaloids, anti-proliferative agents, and combinations thereof. Other bioactive agents of similar or different activities and applications are also encompassed. All biological agents are either commercially available or may be prepared by methods known in the art.

Having now generally described the invention, the same will be better understood by reference to certain specific examples, which are included herein for purposes of illustration only, and are not intended to be limiting of the invention or any embodiment thereof, unless so specified.

EXAMPLES

Example 1

Preparation of IL-2 for Administration

Recombinant human IL-2 (R-Met-HU IL-2 (Ala 125 or rIL-2) was obtained from Amgen (Thousand Oaks, Calif.).

Each 2 ml vial contained approximately 0.4 mg/ml of recombinant IL-2 (rIL-2) in 1.1 ml $H_2O$. The rIL-2 used for the study had a specific activity of $9 \times 10^6$ units/mg protein. All dosages for the study were calculated as International Units (IU), using a specific activity of $15 \times 10^6$ IU/mg protein.

Each vial was diluted to 50% strength with 5% dextrose in water. All individuals in the study received the rIL-2 daily dose in pre-measured syringes, which were kept refrigerated until use.

Example 2

Profile of Patients Selected for First Clinical Trial

Individuals over the age of 18 were eligible for enrollment in the trial if they tested positive for HIV-reactive antibodies, if they were HIV p24 antigen negative, and if they had no concurrent opportunistic infections. In addition, the criteria for eligibility included an absolute CD4+ T-cell count of between 200 and 500 cell/mm³ and being on nucleoside-analogue antiretroviral medication (e.g. AZT, 3TC, ddI, d4T) for at least one month prior to starting IL-2 therapy.

Any individual that had any chronic illness unable to be controlled by medication, pregnant or nursing, or had any history of malignancy was excluded. Hematologic and biochemical criteria utilized for excluding individuals included: total bilirubin >5 times normal, AST >90 IU, creatinine >2.0 mg/dl, neutrophils <100/mm³, hemoglobin <10 mg/dl, platelets <75,000/mm³.

14 individuals were enrolled, who had a mean age of 37 years (range 28–48). The mean time of known HIV infection prior to entrance in the study was 7 years. Before initiation of IL-2 therapy, the mean CD4+ T-cell count was 338 (range 202–495). The group was homogeneous with respect to leukocyte and differential counts, and there were no differences in these parameters among the subjects who were given different IL-2 doses. Twelve of the 14 individuals enrolled had been taking anti-retroviral nucleoside analogue medication for at least 3 months. Two subjects began anti-nucleoside medication 6 weeks prior to initiation of IL-2 therapy.

Based upon an expected rate of decrease of about 80 CD4 T-cells/mm³ per year, the individuals are expected to lose on the average 40 cells/mm³ over a period of six months.

Example 3

Initiation of 6-month Clinical Trial (First Clinical Trial)

On the first day of therapy, all individuals participating in the study were admitted to the hospital. Each individual was given the initial subcutaneous injection of IL-2 and, then, frequent blood samples were taken for the first 24 hours for IL-2 to conduct pharmacokinetic studies. All subjects then received instructions on the self-administration of IL-2 by subcutaneous injection, and were seen subsequently on an out-patient basis weekly for 6 weeks, and then biweekly for the 6 month study period.

Example 4

Doses and Regimes for 5 Dose Groups

Group 1: 125,000 rIL-2/m²/day

Six individuals self-administered 125,000 IU (8.3 μg) rIL-2/m²/day. Two of the individuals had medical histories of mild allergic asthma, and an increase in severity of their asthma symptoms was correlated with each IL-2 inoculation. Therefore, the administration of IL-2 was stopped, and the cessation of IL-2 therapy resulted in the attenuation of symptoms. Subsequently, the IL-2 dose was reduced by 50% for these 2 individuals to 62,500 IU (4.15 μg) rIL-2/m²/day.

The other 4 subjects, receiving 125,000 IU (8.3 μg) rIL-2/m²/day, completed the course (6 months) of therapy without any detected toxicity.

Group 2: 62,500 IU rIL-2/m²/day

Two individuals self-administered 62,500 IU (4.15 μg)rIL-2/m²/day for 6 months (see, Group 1). Although the 2 individuals had side effects at a higher dose, (125,000 IU), no recurrence of the asthma symptoms was observed at this does, and the individuals completed the study without untoward effects.

Group 3: 250,000 IU rIL-2/m²/day

Eight individuals started self-administration of 250,000 IU (16.7 μg)rIL-2/m²/day.

Two of the 8 individuals experienced fever (38.5° C.), myalgia and fatigue, with the onset of systemic symptoms occurring after 4 to 5 days of inoculation, and 6 to 8 hours after each IL-2 injection. Their dose was, thus, decreased to 187,500 IU (12.5 μg) rIL-2/m²/day. The 2 individuals tolerated the lower dose throughout the 6 months of therapy without any further side effects.

The remaining 6 individuals from Group 3 were administered 250,000 IU (16.7 μg)rIL-2/m²/day, and completed the 6 months of therapy without any significant systemic symptoms.

Group 4: 187,500 IU rIL-2/m²/day

The administration of the drug was stopped in the two individuals experiencing fever, myalgia and fatigue after 4 to 5 days of inoculating 250,000 IU rIL-2/m²/day, and 6 to 8 hours after each rIL-2 injection.

Their dose was decreased to 187,500 IU (12.5 μg) rIL-2/m²/day, and they underwent a full course of self-administration at this dose. These two individuals tolerated the lower dose throughout the 6 months of therapy without any side effects.

Group 5: 500,000 IU rIL-2/m²/day

Four subjects received 500,000 IU (33 μg) rIL-2/m²/day IL-2. All the individuals treated at this dose developed systemic symptoms after 4 to 5 days of injections, and were unable to undergo further treatment at this dose level. The treatment was, thus, discontinued.

Example 5

Determination of Toxicity during First Clinical Trial

Toxicity was defined as two consecutive abnormal values found for any one individual. Dose limiting toxicity (DLT) was defined as ≧WHO (World Health Organization) grade 1 toxicity, as shown in Table 2 above. If, and when, DLT occurred in any one individual, treatment was withheld from that particular individual until the toxic symptoms or signs resolved. Treatment was then resumed at an IL-2 dose midway between the previous dose level and the current dose (the dose was halved). The objective was to achieve a dose that was non-toxic but that would permit each subject to carry out normal daily activities.

Example 6

Determination of IL-2 Plasma Concentration

Plasma IL-2 concentrations were determined by ELISA (Endogen, Inc., Boston, Mass.), according to the manufacturer's specification. The lower limit of detection of IL-2 in plasma was 0.5 pM (7.5 pg/ml).

Low, but detectable levels of IL-2 were measurable in 11 of the 14 patients before treatment with IL-2 was started. The mean plasma IL-2 concentration of the samples was 2.5±0.6 pM SEM (range 0.5 to 8.4 pM).

Example 7

Pharmacokinetic Studies for First Clinical Trial

The IL-2 plasma concentration was determined at frequent intervals over the first 24 hours after each dose increment was administered. A marked increase in the detectable IL-2 plasma level was observed when following the time course at a dose of 250,000 IU/m² when compared with the profile obtained at a dose of 125,000 IU/m². At the lower dose level, the peak IL-2 concentration attained was only about 3–4 pM. A doubling of the dose resulted in greater than 5-fold increase in the peak IL-2 plasma concentration, to 25 pM.

At these doses, concentrations of IL-2 that saturate about 50% of the high affinity receptors (about 10 pM) were detectable even 8 hours after the injection, and increased IL-2 plasma levels were still measurable 24 hours later. Thereafter, the measurement of trough IL-2 plasma levels just prior to the next dose revealed that further daily doses of IL-2 did not result in gradually increasing plasma IL-2 levels.

Example 8

Determination of Circulating Leukocyte Count for Individuals in First Clinical Trial The determinations of leukocyte types and concentrations were performed by tricolor flow cytometry using monoclonal antibodies directly conjugated with fluorochromes as described by Stewart and Stewart (Stewart, C. and Stewart, S., "Cell Preparation for the Identification of Leukocytes", Darynkiewicz Z., Robinson, J., Crissman H., Eds., in Methods in Cell Biology, pp. 39–60 (1994)).

Example 9

Effects of IL-2 Therapy on Leukocyte Production by Individuals in First Clinical Trial Six individuals enrolled in the trial received <125,000 IU rIL-2/m²/day, which lead to subsaturating IL-2 levels. Eight individuals received 187,500 IU rIL-2/m² and 250,000 IU/m², having near saturating peak plasma rIL-2 levels. The data on leukocyte production obtained from these two groups were analyzed separately and compared with one another.

Over the six month period of treatment, no significant changes were observed in absolute neutrophil counts, CD8+ T-cell counts or B-cell counts from values obtained prior to rIL-2 therapy for either group. Nor were there significant differences in levels of circulating white blood cells between the two treatment groups during therapy.

A marked increase in the mean concentration of circulating NK cells, however, was observed in the group receiving a daily doses of 250,000 IU rIL-2/m² (Groups 3). After six months of treatment, the NK cell count or concentration had increased 7-fold when compared to the count prior to initiation of therapy. No significant change was observed in the NK cell count in the group that received <125,000 IU/m²/day (Group 4).

Linear trends in NK cell counts occurring during the trial period were calculated for each treatment group as a mean of the slopes obtained for each individual subject using data obtained at monthly intervals. A mean monthly gain of 50 cells/mm$^3$ was observed in the group that received 250,000 IU rIL-2/m$^2$/day (Group 3), compared with a mean monthly gain of 9 cell/mm$^3$ for the group that received <125,000 IU rIL-2/m$^2$/day (Group 4) ($p=0.04$).

The concentration of circulating eosinophils was also observed to change. An increased eosinophil count was observed after only 2 weeks of rIL-2 inoculations, and peak levels occurred at 1 month after inoculation, with a subsequent decrease toward baseline within 2 months. There was a greater increase in circulating eosinophils at the 187,500 and 250,000 IU rIL-2/m$^2$/day doses than at the lower doses. Thus, with this rIL-2 preparation, a greater than 9-fold increase in eosinophils occurred at the latter doses after 1 month of therapy, compared with a lesser than 3-fold increase for the subjects receiving the submaximal doses. In addition, at the the latter doses, the circulating count of eosinophils reached a steady state that was 2- to 3-fold greater than that observed prior to starting the rIL-2 therapy ($t=0$). At the lower rIL-2 doses, the eosinophil count returned to baseline without reaching a steady state.

A rIL-2 dose-dependent change in the concentration of circulating monocytes was also observed. At the lower rIL-2 doses (Groups 1 and 2), the monocyte counts decreased slightly during the study interval. By comparison, at the intermediate and higher doses (Groups 3 and 4), there was an increase in circulating monocytes that peaked after 2 months of rIL-2 treatment, which then remained 2- to 3-fold elevated from baseline for the remainder of the study interval.

At the initiation of the study, the concentration of CD4+ T-cells in the HIV+ individuals was $338\pm26$ cells/mm$^3$ (mean±SEM) as compared with $860\pm150$ cells/mm$^2$ for normal individuals.

A progressive decline in CD4+ T-cells to $275\pm52$ cells/mm$^3$ was observed after six months of therapy at the <125,000 IU rIL-2/m$^2$/day dose (Group 1). Mean monthly changes in CD4+ T-cells were calculated from the linear trends obtained from the mean of the slopes. A mean monthly gain in CD4+ T-cells of 26 cells/mm$^3$ was calculated for the groups receiving the intermediate and higher doses (Groups 3 and 4). A mean monthly loss of 28 CD4+ T-cells/mm$^3$, on the other hand, occurred in the group that received <125,000 IU rIL-2/m$^2$/day (Group 1) ($p=0.01$).

Example 10

Determination of Plasma HIV Concentration

Plasma HIV concentrations were determined at the beginning of the clinical trial of Examples 2 and 3 by branched chain DNA assays as described by Pachl et al. (Pachl et al., J. Acq. Immune Defic. Syndromes and Human Retrovirol. 8:446–54 (1995)). Thereafter, they were sent for assaying to Chiron, Corporation, Emeryville, Calif.

Example 11

Effect of IL-2 Therapy on Plasma HIV Conc. in Individuals in First Clinical Trial The first 6 individuals entered in the study were monitored for plasma HIV RNA levels with a branched chain DNA assay (bDNA) that had a sensitivity of 10,000 viral RNA molecules/ml. Only 2 of these individuals had detectable plasma HIV levels (14 and $20\times10^3$ viral RNA molecules/ml, respectively). The assays of these 2 individuals became negative after initiation of IL-2 treatment and remained so throughout the 6 months of the study.

The plasma HIV levels of the other 4 individuals remained negative during the 6 month study interval.

Subsequent to enrollment of the first 6 individuals, a second generation bDNA assay became available that is significantly more sensitive, and has a lower is limit of detection of 500 HIV RNA molecules/ml. Accordingly, the next 8 individuals enrolled were monitored using the improved bDNA assay. At the initiation of IL-2 therapy, the mean plasma HIV concentration of these 8 individuals was $4428\pm2543$ (SEM) RNA molecules/ml. Over the course of 6 months of IL-2 therapy, the mean HIV concentration fluctuated less than 2-fold, and at the end of the study the mean HIV concentration was not significantly different from that at the initiation of IL-2 treatment ($5150\pm1984$ (SEM) RNA molecules/ml).

Example 12

Clinical Trial of IL-2 Immunotherapy of Asymptomatic HIV+ Individuals Extending beyond One Year This experiment demonstrates that the present maintenance (chronic) IL-2 therapy utilized in the first trial described in Examples 2 and 3 above, may be administered to individuals for prolonged periods of time in excess of 2 years and beyond, with extended beneficial results. To extend the chronic administration of IL-2 beyond 6 months, 10 asymptomatic HIV+ individuals are recruited to self-administer IL-2 subcutaneously, in daily doses ranging from 187,500 to 250,000 IU/m$^2$ (12.5–16.7 $\mu$g/m$^2$) body surface area (or 4,000 to 5,350 IU/kg body weight) for at least 12 months. Subjects are eligible for study if they test positive for HIV-reactive antibodies, and if they have plasma HIV detectable by the branched-chain DNA (bDNA) assay of Pachl et al. (1995), suprs, which has a lower limit of detection of 500 RNA equivalents/ml. Each individual receives antiviral medication concomitantly with the IL-2 therapy consisting of zidovudine (AZT, 600 mg/d), and lamivudine (3TC, 300 mg/d) throughout the 12 month IL-2 treatment interval. Each individual is monitored monthly for clinical signs and symptoms of adverse effects, and for laboratory evidence of organ system dysfunction. Immune system parameters studied, include cutaneous tests for delayed-type-hypersensitivity (DTH) to common recall antigens, including Candida albicans, dermatophyton, trichophyton, mumps virus, and tetanus toxoid. Circulating white blood cells (WBC) are monitored by flow cytometry, with particular attention to changes in the concentration of lymphocytes, such as T-cells, B-cells, and natural killer (NK) cells, monocytes, and polymorphonuclear leukocytes (PMNs), including neutrophils, basophils and eosinophils. T cell subsets identified by the CD4 and CD8 surface markers are noted, along with surface markers indicative of activation, including the receptor IL-2R $\alpha$ chain, and IL-2R $\beta$ chain, MHC Class II, CD40 Ligand (CD95), and Fas ligand.

35 subjects participate in the study. Linear trends in cell counts and plasma HIV concentration over time are calculated by computing linear regression slopes separately for each patient. The average slope for the study population is compared with baseline values using a student's T test.

Example 13

Comparison of Joint AZT/IL-2 Therapy with Treatment with AZT Alone of Asymptomatic HIV+ Individuals This comparison between the results obtained in the randomized AZT plus low doses of IL-2 immunotherapy clinical trial described in Examples 2 and 3, and a similar study conducted solely with AZT, demontrates that the combined long term therapy affords an unexpected synergy over the AZT alone treatment.

The Concorde is a double blind randomized study on the administration of AZT to asymptomatic HIV+ individuals (The Lancet 343: 871–881 (1994)). The recruited individuals were divided into two groups, an early administration group and a second group where AZT administration was started after the individual's T-cell count fell below a certain figure or the individual developed ARC or AIDS. AZT was administered at a dose of 250 mg four times per day to 877 asymptomatic HIV+ individuals and a control group of 872 individuals were given a placebo. The individuals were followed-up until death or for 3 years. Of the placebo group, 418 started AZT treatment at some point in the trial, 174 after developing ARC or AIDS, and the remainder based on their low CD4 cell counts. No statistical difference was observed between the two regimes in the results observed.

As described in Examples 2 and 3 above, the combination of anti-viral treatment with immunotherapy with the present low doses of IL-2 provides unexpected benefits when compared with anti-viral therapy alone. While artisans with skill in the art have been utilizing substantially higher doses of IL-2 for therapy, the present low dose regime in combination with an anti-viral drug produces anti-viral effects with a concomitant stimulation of the immune system, in the absence of toxicity WHO Grade 1 or higher. Thus, the combined therapy precludes the onset of immunodeficiency and the clinical diagnosis of ARC and AIDS without the toxicity observed with other treatments.

Moreover, in the Concord study, after the first 6 months of therapy the concentration of circulating CD4+ T-cells was unchanged from base line in both, the AZT-treated and in the placebo-treated, groups. On the basis of the clinical trial reported herein in Examples 2 and 3 above, the present immunotherapy produced an increase in the concentration of circulating CD4+ T-cells of about 26 cells/mm$^3$ per month.

Example 14

IL-2 Immunotherapy of Normal Individuals

This experiment demonstrates the beneficial effect of IL-2 when self-administered in low doses by normal individuals for fighting infections, such as the common cold, the grippe, and the flu.

Group I: IL-2 Immunotherapy 10 normal individuals are recruited into the study and given individually sealed 250,000 IU/m$^2$ IL-2 daily doses for self-administration, when signs of a cold, fever, myalgia, cough, or rhinitis appear. The individuals self-administer the IL-2 before and during the course of the infection and resolution of the symptoms of the cold or flu.

Group 2: Placebo 10 normal individuals are recruited and given sealed daily dose of placebo for self-administration as in group 1.

All individuals in this study report on the development of their infections, symptoms, including dates, and severity, on a scale of 1 to 10, from the mildest to most severe symptoms, including temperature, ambulatory ability, body aches, nasal mucosity, fatigue, cough, nausea, and vomiting. Results are recorded twice daily until the resolution of all symptoms. Individuals are monitored 3 times per week as ambulatory patients by a trained investigator.

The individuals in Group 1 greatly benefit from the treatment in comparison with Group 2, particularly with regard to the rate of onset of symptoms, and the rate of resolution of symptoms.

Example 15

Confirmation of Potentiation of Combined IL-2/ Anti-viral Therapy vs. Antiviral Therapy Alone This experiment confirms a synergistic effect of antiviral therapy plus IL-2 immunotherapy, as shown by improved immune function. When administered to HIV+ asymptomatic individuals, antiviral therapy alone decreases CD4+ T-cell destruction. On the other hand, IL-2 immunotherapy is shown to stimulate CD4+ T-cell production.

50 asymptomatic HIV+ individuals are recruited early in the course of HIV infection, with CD4+ T-cell counts >500 cells/mm$^3$ of blood. The individuals are randomized to receive antiviral therapy vs. antiviral therapy plus IL-2 immunotherapy. 25 individuals are placed in each treatment group.

Group 1: Anti-viral Therapy Alone

Antiviral therapy consists of a combination of the nucleoside analogues zidovudine (AZT, 600 mg/day), lamivudine (3TC, 300 mg/day), and the protein inhibitor invirase (600 mg/day).

Group 2: Combined Anti-viral/IL-2 Therapy 25 individuals receive anti-viral therapy as in Group 1 plus IL-2 over the same period of time. The IL-2 is self-administered daily by subcutaneous injection at 250,000 IU IL-2/m$^2$ (16.7 $\mu$g/m$^2$).

All individuals are monitored as detailed above, for clinical signs and symptoms of toxicity, and laboratory tests for functional abnormalities of the major organ systems are done. Plasma HIV levels are determined by the bDNA assay of Pachl et al. (1995), supra, and immunological tests conducted include cutaneous tests for delayed-type hypersensitivity (DTH), and white blood cell (WBC) enumeration by flow cytometry.

For statistical analysis, linear trends in cell counts and HIV plasma levels over time are calculated by computing linear regression slopes separately for each subject, and then the average slopes for each treatment group is compared using the Students' T test. Following 6 months of therapy, each treatment group is crossed-over to the alternative therapy, and the study continues for an additional 6 months.

Example 16

Clinical Trial with IL-2 Immunotherapy on Individuals with Congenital and Acquired Immunodeficiencies 10 individuals suffering from congenital immunodeficiencies, particularly those due to an inability to produce IL-2, and individuals suffering from acquired immunodeficiencies that are not secondary to HIV infection, such as common variable immunodeficiencies, and immunodeficiencies following cytotoxic treatments for cancer (e.g., chemotherapy and radiotherapy), are recruited for IL-2 immunotherapy providing chronic immune stimulation with IL-2. These individuals self-administer IL-2 treatment protocols for 6 months to 1 year, similar to those employed for asymptomatic HIV+ individuals, shown in Example 3 above, except that they do not receive AZT. The daily dose self-injected is 250,000 IU IL-2/m$^2$ body surface. Noticeable improvement is noticed with respect to the initial symptomatology, including suceptibility to infections, particularly those caused by opportunistic organisms, and by a reduced requirement for other immune enhancing therapies, such as the administration of i.v. immunoglobulin.

Example 17

Clinical Trial with IL-2 Immunotherapy for Individuals Suffering from Microbial Infections This experiment has been set up to demonstrate that microbial infections, especially chronic infections, benefit from low dose, chronic IL-2 immune stimulation. Examples of microbial infections are, for example, those due to viruses (e.g., hepatitis viruses), mycobacteria (e.g., tuberculosis, especially multi-drug-resistant M. tuberculosis), fungi (e.g., candidiasis, aspergillosis, histoplasmosis, coccidiomycosis, and nocardiosis), and parasites (e.g., toxoplasmosis, pneumocystosis), benefit from chronic immune stimulation.

10 individuals are recruited into this study, which are afflicted by a microbial infection, and evidencing low immune system activity. Each individual self-administers 250,000 IU IL-2/m$^2$/day over a period of up to 6 months to 1 year and, depending on the severity and criticality of symptoms, periodic tests are conducted as described in Example 16 above. Amelioration of overall symptoms associated with increased immune response is observed.

Example 18

Clinical Trial with IL-2 Immunotherapy for Cancer Patients without Residual Detectable Malignancy after Primary Anti-cancer Therapy This experiment is conducted to demonstrate that chronic IL-2 immunotherapy is beneficial for individuals afflicted with various cancers, such as malignant melanoma, renal cell carcinoma, breast carcinoma, non-Hodgkins lymphoma, Hodgkins lymphoma, leukemia, and multiple myeloma. A daily maintenance dose of 250,000 IU/m$^2$ is self-administered by each individual, and tests are conducted as described above in Examples 15 and 16.

10 individuals are recruited into this study, all of whom have received a course of anti-cancer therapy, and have been determined not to have any malignant cells or tissue by standard tests, such as x-ray, CT scans or blood tests. The individuals are divided randomly into two groups.

Group 1: Placebo 5 individuals self-administer placebo without IL-2 or other medication.

Group 2: IL-2 Immunotherapy

Five individuals self-administer 250,000 IU IL-2/m$^2$ per day.

The overall beneficial effect is determined by the duration of the interval the individual remains tumor-free and by the individual's survival.

Example 19

IL-2 Therapy Administered by Other Routes

This experiment has been designed to demonstrate that chronic IL-2 immunotherapy, in accordance with this invention, is beneficial without eliciting substantial toxicity WHO Grade 1 or higher, when administered by routes other than injection.

Ten individuals are recruited into the study, including normal individuals, individuals afflicted with cancer, and invididuals infected with HIV and other microbial infections, and congenital and acquired immunodeficiencies. All individuals are matched with at least one corresponding individual, who self-administered IL-2 by injection under similar conditions.

All individuals are instructed as described in Example 3 above to self-apply a patch or to inhale a daily dose of 250,000 IU/m$^2$ of IL-2 for 6 months to 1 year. All individuals in this study report on their progress, including symptoms, severity, and others, and date of occurrence, scoring on a scale of 1 to 10, from the mildest to the most severe symptoms, including fever, fatigue, myalgia, nausea, and vomiting. The results obtained are similar to those when IL-2 immunotherapy is conducted by injection.

Example 20

Therapy Utilizing Different Forms of the Agent

This experiment is conducted to show that immunotherapy with analogs of IL-2 afford to the individuals results similar to immunotherapy with IL-2 itself, in terms of benefits observed in the substantial absence of toxicity WHO Grade 1 or higher.

Ten individuals are recruited into this study, including normal individuals, individuals afflicted with cancer, HIV and other microbial infections, and congenital and acquired immunodeficiencies.

A dose of derivatized IL-2 corresponding to 250,000 IU/m$^2$ of IL-2 is self-administered daily by subcutaneous injection by each individual over a period of 6 months to 1 year. A dose of mutated IL-2 corresponding to 250,000 IU/m$^2$ of IL-2 is self-administered daily by each individual for a period of six months. A dose of mutated X-IL-2 corresponding to 250,000 IU/m$^2$ of IL-2 is self administered daily by each individual for a period of six months. Tests and reports are as described above. Each individual is matched with an individual receiving recombinant IL-2 by injection as described in Example 3 above. Results which are similar to those obtained with recombinant IL-2 immunotherapy are observed.

Having now generally described the invention, as well as by reference to the examples, an artisan will understand that many variations may be applied that are within the confines of the invention.

What is claimed as novel and unobvious in Letters Patent of the United States is:

1. A method of chronic stimulation and/or maintenance of immune response, comprising the administration or application or self-application to a subject or the subject's self-administration of a composition comprising an agent selected from the group consisting of natural and recombinant IL-2, pharmaceutically-acceptable fusion proteins of natural and recombinant IL-2, PEG-natural and -recombinant IL-2, lipid-conjugated natural and recombinant IL-2, therapeutic agent-linked natural and recombinant IL-2, reduced natural and recombinant IL-2, glycosylated natural and recombinant IL-2, non-glycosylated natural and recombinant IL-2, and mixtures thereof, for a period greater than three months in an amount and under conditions effective to release about 100,000 to about 500,000 IU IL2/m$^2$ body surface/day or equivalent to about 1,000 to about 500,000 IU IL-2/m$^2$ body surface/day, the agent having a specific activity or 15×10$^6$ IU/mg protein.

2. The method of claim 1, wherein the composition is administered, applied, self-administered, or self-applied by subcutaneous, intramuscular, intradermal, intralymphatic, intratumor, transdermal, intracavitary, transbuccal, transpulmonary, oral, intranasal, transmucosal, intravaginal, intraanal, intrabuccal, or sublingual administration or application, by inhalation, or by implant.

3. The method of claim 1, wherein the composition is self-administered.

4. The method of claim 1, wherein the composition comprises a controlled release composition.

5. The method of claim 1, further comprising adjusting the amount of the agent administered, applied, self-administered, or self-applied by monitoring the blood concentration of the agent, the % saturation of the high affinity IL-2 receptors, or the blood count of at least a cell type selected from the group consisting of circulating lymphocytes, monocytes, and polymorphonuclear leukocytes.

6. The method of claim 1, wherein the subject is a normal subject or a subject afflicted with a condition associated with a viral, bacterial, fungal, and parasitic microorganism, a congenital or acquired immunodeficiency, or a malignancy.

7. The method of claim 6, wherein the subject is HIV seropositive human; and the composition is administered applied, self-administered, or self-applied in an amount and under conditions which substantially avoid increasing the count of circulating microorganisms.

8. The method of claim 1, wherein the subject is an animal.

9. The method of claim 8, wherein the animal is a human.

10. The method of claim 1, wherein the amount of the agent administered, allied, self-administered, or self-applied is effective to elevate the count of at least one blood cell type selected from the group consisting of circulating lymphocytes, monocytes, pa polymorphonuclear leukocytes.

11. The method of claim 10, wherein the amount of the agent administered, applied, self-administered, or self-applied is effective to elevate the count of at least one blond cell selected from the group consisting of circulating T-cells, B-cells, NK cells, monocytes, eosinophils, neutrophils, basophils and antigen-presenting cells.

12. The method of claim 1, wherein the administered, applied, self-administered or self-applied composition is in the form of a powder, a tablet, a capsule, a dragee, a cream, a solution, a suspension, an emulsion, a gel, a spray, a liposome or other micelle, or combinations or mixtures thereof, and formulated prior to administration, application, self-administration or self-application.

13. The method of claim 1, wherein the administered or self-applied composition is in solid form, and formulated prior to administration, application, self-administration, or self-application.

14. The method of claim 13, wherein the administered, applied self-administered or self-applied composition is in lyophilized form.

15. The method of claim 1, wherein the administered, applied, self-administered or self-applied composition is in liquid form.

16. The method of claim 1, wherein the composition is administered, applied, self-administered, or self-applied by means of an inhalant.

17. The method of claim 1, wherein the agent is administered, applied, self-administered, or self-applied as a topical composition, further comprising a carrier or diluent for the agent suitable for topical delivery and an ingredient selected from the group consisting of buffers, salt forming acids and bases, perfumes, colorants, emollients, adjuvants, single or multiple enteric coatings, copolymers, microporous or semi-permeable membranes, enzyme inhibitors, mucoadhesives, chelating agents, particulate systems, viral envelope proteins, liposomes and other micelles, emulsifiers, lipoproteins and other fatty acid derivatives, surfactants, bile salts, hydrophilic, neutral, and hydrophobic polymers and co-polymers, hydrogels, biodegradable polymers and co-polymers, and an additional bioactive agent selected from the group consisting of additional lymphokines or cytokines , and fusion proteins of the lymphokines or cytokines, anti-inflammatories, anti-bacterial, anti-viral, anti-fungal, anti-parasitic, anti-metabolic, anti-inflammatory, vasoactive, anti-neoplastic, bronchodilating, local anesthetic, immunomodulating, growth promoting and regenerating agents, enzymatic, hormonal agents, neurotransmitters, and cell receptor proteins and ligands.

18. The method of claim 17, wherein the composition is in the form of a cream, an ointment, a solution, a gel, a powder, a suspension, an emulsion, encapsulated particles or mixtures thereof.

19. The method of claim 17, wherein the agent is present in an amount of about 0.0001 to 50 wt % of the composition.

20. The method of claim 17, wherein the composition comprises a controlled release composition.

21. The method of claim 17, wherein the composition is administered by a transdermal delivery device comprising, in a sterile container, a solid support; and a compartment provided in the solid support, the compartment comprising a solution or suspension of the composition, and having one side permeable thereto; whereby when the permeable side of the compartment is placed in contact with an area of a subject's dermis a desired amount of the agent passes from the device onto, and through, the dermis of the subject, over a pre-determined period of time.

22. The method of claim 21, wherein the device comprises a unit dose of the agent.

23. The method of claim 21, wherein the device further comprises a cover placed on the permeable side of the container; the cover being substantially impermeable to the solution or suspension and removable prior to administration, application, or self-application.

24. The method of claim 21, wherein the device is an electrotransport device, further provided with donor and counter electrodes; external power source and control circuitry; wherein the solution or suspension further comprises electroconducting agents, and when the permeable side of the device is placed in contact with an area of the subject's dermis and an electric field is applied to the electrodes, a desired amount of the agent passes from the device onto, and through, the dermis of the subject, over a pre-determined period of time.

25. The method of claim 21, wherein the device is an ultrasound device, further provided with ultrasound transducer, external power source and control circuitry; wherein when the permeable side of the device is placed in contact with an area of the subject's dermis and an electric field is applied to the ultrasound generator, a desired amount of the agent passes from the device onto, and through, the dermis of the subject, over a pre-determined period of time.

26. The method of claim 20, wherein the agent is released by an implant, the implant comprising an amount effective to release the desired amount of the agent over a predetermined period of time.

27. The method of claim 1, further comprising administering or applying to the subject or having the subject self-administer or self-apply a bioactive agent selected from the group consisting of additional lymphokines or cytokines, fusion proteins of the lymphokines or cytokines, anti-inflammatory, anti-bacterial, anti-viral, anti-fungal, anti-parasitic, anti-metabolic, vasoactive, anti-neoplastic, bronchodilating, local anesthetic, immunomodulating, growth promoting, regenerating, enzymatic and hormonal agents, neurotransmitters, and cell receptor proteins and ligands.

28. The method of claim 27, wherein the subject is administered, applied, self-administered, or self-applied the agent and a bioactive agent selected from the group consisting of anti-bacterial agents, anti-fungal agents, anti-parasitic agents and anti-viral agents.

29. The method of claim 28, wherein tie bioactive agent comprises one or more anti-viral agents.

30. The method of claim 29, wherein the anti-viral agents are selected from the group consisting of nucleotide analogues and protease inhibitors.

31. The method of claim 30, wherein the subject is administered, applied, self-administers or self-applies, one or more anti-viral agents selected from the group consisting of zidovudine (AZT), 2',3'-dideoxyinosine (ddI), 3'-azido-2', 3'-dideoxythymidine, d4T, acyclovir, 1,3-dihydro-2-propoxy-methyquanine (gancyclovir), ribavirin, dideoxycytidine (ddC), lamivudine (3TC), and enzyme inhibitors.

32. The method of claim 31, wherein the subject is administered or applied, self-administers or self-applies one or more enzyme inhibitors, and the enzyme inhibitors comprise protease inhibitors.

33. The method of claim 32, wherein the protease inhibitors are saquinovir or invirase.

34. The method of claim 31, wherein the subject is administered or applied, self-administers or self-applies one or more anti-viral agents, and the anti-viral agents are selected from the group consisting of zidovudine (AZT), lamivudine (3TC), d4T, invirase and combinations and mixtures thereof.

35. The method of claim 34, wherein the anti-vital agent combinations administered, applied, self-administered or self-applied comprise
zidovudine (AZT), lamivudine (3TC), and d4T, or
zidovudine (AZT), lamivudine (3TC), and invirase.

36. The method of claim 35, wherein
the anti-viral agent combination administered, applied, self-administered or self-applied comprises zidovudine (AZT), lamivudine (3TC), and d4T, and
zidovudine is administered, applied, self-administered or self-applied at about 600 mg/day, lamivudine (3TC) at about 300 mg/day, and invirase at about 600 mg/day.

37. The method of claim 28, wherein the subject is administered, applied, self-administers or self-applies one or more bioactive agents.

38. The method of claim 37, wherein the bioactive agents comprise anti-bacterial agents.

39. The method of claim 37, wherein the anti-bacterial agents comprise antibiotics.

40. The method of claim 39, wherein the antibiotics are selected from the group consisting of pentamidines, trimethoprim-sulfamethoxazole, sulfonamides, penicillins, cephalosporins, aminoglycosides, tetracyclines, chloramphenicols, and combinations and mixtures thereof.

41. The method of claim 37, wherein the bioactive agents comprise anti-fungal agents.

42. The method of claim 41, wherein the anti-fungal agents are selected from the group consisting of flucytosine, amphotericin B, fluconazole, griseofulvine, and combinations and mixtures thereof.

43. The method of claim 37, wherein the bioactive agents comprise anti-parasitic agents.

44. The method of claim 43, wherein the anti-parasitic agents are selected from the group consisting of pyrimethamine, quinacrine, thiabendazole, levamisol, and combinations and mixtures thereof.

45. The method of claim 37, wherein the bioactive agents comprise anti-metabolic agents.

46. The method of claim 45, wherein the anti-metabolic agents are selected from the group consisting of purine analogues, folic acid analogues, pyrimidine analogues, and combinations and mixtures thereof.

47. A method of chronic stimulation and/or maintenance of immune response, comprising the administration or application to a subject in need of treatment or the subject's self-administration, or self-application of an agent selected from the group consisting of natural and recombinant IL-2, pharmaceutically-acceptable fusion proteins of natural or recombinant IL-2, PEG-natural and recombinant IL-2, lipid-conjugated natural and recombinant L-2, therapeutic agent-linked natural and recombinant IL-2, reduced natural and recombinant IL-2, glycosylated natural and recombinant IL-2, non-glycosylated natural and recombinant IL-2, and mixtures thereof, for a period greater than three months in an amount and under conditions effective to release about 100,000 to about 500,000 IU IL-2/m$^2$ body surface/day or equivalent to about 100,000 to about 500,000 IU IL-2/m$^2$ body surface/day, the agent having a specific activity of $15 \times 10^6$ IU/mg protein.

48. A method of increasing and/or maintaining the count of circulating blood cells selected from tie group consisting of lymphocytes, monocytes, and polymorphonuclear leukocytes, comprising the administration or application to a subject or the subject's self-administration, or self-application of a composition comprising an agent selected from the group consisting of natural and recombinant IL-2, pharmaceutically acceptable Fusion proteins of natural and recombinant IL-2, PEG-IL-2 natural and recombinant, lipid-conjugated natural and recombinant IL-2, therapeutic agent-linked natural and recombinant IL-2, reduced natural and recombinant IL-2, glycosylated natural and recombinant IL-2, non-glycosylated natural and recombinant IL-2, and mixtures thereof, for a period greater than three months in an amount and under conditions effective to release about 100,000 to about 500,000 IU IL-2/m$^2$ body surface/day or equivalent to about 100,000 to about 500,000 IU IL-2/m$^2$ body surface/day, the agent having a specific activity of $15 \times 10^6$ IU/mg protein.

49. The method of claim 48, wherein the composition further comprises an ingredient selected from the group consisting of carriers, diluents, buffers, salt forming acids and bases, perfumes, colorants, emollients, adjuvants, single or multiple enteric coatings, copolymers, microporous or semi-permeable membranes, enzyme inhibitors, mucoadhesives, chelating agents, particulate systems, viral envelope proteins, liposomes and other micelles, emulsifiers, lipoproteins and other fatty acid derivatives, surfactants, bile salts, hydrophilic, neutral, and hydrophobic polymers and co-polymers, hydrogels, biodegradable polymers and co-polymers, and anti-inflammatories, an additional bioactive agent selected from the group consisting of additional lymphokines or cytokines, and fusion proteins of the lymphokines or cytokines, anti-inflammatories, anti-bacterial, anti-viral, anti-fungal, anti-parasitic, anti-metabolic, anti-inflammatory, vasoactive, anti-neoplastic, bronchodilating, local anesthetic, immunomodulating, growth promoting and regenerating agents, enzymatic, hormonal agents, neurotransmitters, and cell receptor proteins and ligands.

50. The method of claim 48, wherein the subject is selected from the group consisting of normal subjects and subjects afflicted with a condition associated with a viral, bacterial, fungal, and parasitic microorganism, a congenital and acquired immunodeficiency, and a malignancy.

51. The method of claim 50, wherein the subject is an HIV seropositive human, and the agent is administered, applied, self-administered, or self-applied in an amount and under conditions which avoid increasing the count of circulating microorganisms.

52. A method of administering or applying to a subject an agent selected from the group consisting of natural and recombinant IL-2, pharmaceutically acceptable fusion proteins of natural and recombinant IL-2, PEG-IL-2 natural and recombinant, lipid-conjugated natural and recombinant IL-2, therapeutic agent-linked natural and recombinant IL-2, reduced natural and recombinant IL-2, glycosylated natural and recombinant IL-2, non-glycosylated natural and recombinant IU-2, and mixtures thereof in the absence of toxicity grade 1 or higher, comprising the administration, application, self-administration, or self-application for a period greater than three months of a composition comprising the agent in an amount and under conditions effective to release about 100,000 to about 500,000 IU IL-2/$m^2$ body surface/day or equivalent to about 100,000 to about 500,000 IU IL2/$m^2$ body surface/day, the agent having a specific activity of $15 \times 10^6$ IU/mg protein.

53. The method of claim 52, wherein the subject is selected from the group consisting of normal subjects and subjects afflicted with a condition associated with a viral, bacterial, fungal, and parasitic microorganism, a congenital and acquired immunodeficiency, and a malignancy.

54. The method of claim 53, wherein the subject is an HIV seropositive human, and the agent is administered, applied, self-administered, or self-applied in an amount and under conditions which avoid increasing the count of circulating microorganisms.

55. A method of administering or applying to a subject an agent selected from the group consisting of natural and recombinant IL-2, pharmaceutically acceptable fusion proteins of natural and recombinant IL-2, PEG-IL2 natural and recombinant, lipid-conjugated natural and recombinant IL-2, therapeutic agent-linked natural and recombinant IL-2, reduced natural and recombinant IL-2, glycosylated t in a IL-2, non-glycosylated natural and recombinant IL-2, and mixtures thereof, comprising the administration, application, self-administration, or self-application for a period greater than three months of a therapeutic product comprising the agent, which when administered or applied lo a subject releases an amount of the agent over a predetermined period of time effective to release about 100,000 to about 500,000 IU IL-2/$m^2$ body surface/day or equivalent to about 100,000 to about 500,000 IU IL-2/$m^2$ body surface/day, the agent having a specific activity of $15 \times 10^6$ IU/mg protein.

56. The method of claim 55, wherein the product further comprises an ingredient selected from the group consisting of carriers, diluents, buffers, salt forming acids and bases, perfumes, colorants, emollients, adjuvants, single or multiple enteric coatings, copolymers, microporous or semipermeable membranes, enzyme inhibitors, mucoadhesives, chelating agents, particulate systems, viral envelope proteins, liposomes and other micelles, emulsifiers, lipoproteins and other fatty acid derivatives, surfactants, bile salts, hydrophilic, neutral, and hydrophobic polymers and co-polymers, hydrogels, biodegradable polymers and co polymers, and anti-inflammatories, an additional bioactive agent selected from the group consisting of additional lymphokines or cytokines, and fusion proteins of the lymphokines or cytokines, anti-inflammatories, anti-bacterial, anti-viral, anti-fungal, anti-parasitic, anti-metabolic, anti-inflammatory, vasoactive, anti-neoplastic, bronchodilating, local anesthetic, immunomodulating, growth promoting and regenerating agents, enzymatic, hormonal agents, neurotransmitters, and cell receptor proteins and ligands.

57. The method of claim 55, wherein the subject is selected from the group consisting of normal subjects and subjects afflicted with a condition associated with a viral, bacterial, fungal, and parasitic microorganism, a congenital and acquired immunodeficiency, and a malignancy.

58. The method of claim 57, wherein the subject is an HIV seropositive human, and the agent is administered, applied, self-administered, or self-applied in an amount and under conditions which avoid increasing the count of circulating microorganisms .

59. The method of claim 29, wherein the subject is a normal subject or a subject afflicted with a condition associated with a viral, bacterial, fungal, and parasitic microorganism, a congenital or acquire immunodeficiency, or a malignancy.

60. The method of claim 59, wherein the subject is an HIV scropositive human; and the composition is administered, applied, self-administered, or self-applied in an amount and under conditions which substantially avoid increasing the count of circulating microorganisms.

\* \* \* \* \*